(12) United States Patent
Tong

(10) Patent No.: US 6,912,414 B2
(45) Date of Patent: Jun. 28, 2005

(54) ELECTRODE SYSTEMS AND METHODS FOR REDUCING MOTION ARTIFACT

(75) Inventor: David A. Tong, San Antonio, TX (US)

(73) Assignee: Southwest Research Institute, San Antonio, TX (US)

(*) Notice: Subject to any disclaimer, the term of this patent is extended or adjusted under 35 U.S.C. 154(b) by 125 days.

(21) Appl. No.: 10/352,204

(22) Filed: Jan. 28, 2003

(65) Prior Publication Data
US 2003/0171661 A1 Sep. 11, 2003

Related U.S. Application Data

(60) Provisional application No. 60/352,202, filed on Jan. 29, 2002.

(51) Int. Cl.[7] ............................................. A61B 5/0408
(52) U.S. Cl. ....................... 600/372; 600/391; 600/509; 600/523
(58) Field of Search ................................ 600/372, 386, 600/391–395, 509, 523

(56) References Cited

U.S. PATENT DOCUMENTS

| 4,274,419 A | 6/1981 | Tam et al. |
| 4,311,152 A | 1/1982 | Modes et al. |
| 4,503,860 A | 3/1985 | Sams et al. |
| 4,538,612 A | 9/1985 | Patrick, Jr. |
| 4,757,817 A | 7/1988 | Healy |
| 5,259,387 A | 11/1993 | dePinto |
| 5,309,909 A | 5/1994 | Gadsby et al. |
| 5,355,883 A | 10/1994 | Ascher |
| 5,445,537 A | 8/1995 | Abyzov |
| 5,458,141 A | 10/1995 | Neil |
| 5,645,063 A | 7/1997 | Straka, Jr. |
| 5,795,293 A | 8/1998 | Carim et al. |
| 5,908,393 A | 6/1999 | Albrecht et al. |
| 5,978,693 A | 11/1999 | Hamilton et al. |
| 2004/0030258 A1 * | 2/2004 | Williams et al. ............ 600/544 |

OTHER PUBLICATIONS

Devlin, Phillip H. et al., "Detecting Electrode Motion Noise in ECG Signals by Monitoring Electrode Impedance," *Computers in Cardiology*, pp. 51–56, 1984.

Thakor, Thakor V. et al., Applications of Adaptive Filtering to ECG Analysis: Noise Cancellation and Arrhythmia Detection, "*IEEE Transactions on Biomedical Engineering,*"pp. 785–794, vol. 38, No. 8, 1991.

* cited by examiner

Primary Examiner—Lee S. Cohen
(74) Attorney, Agent, or Firm—Oliff & Berridge, PLC

(57) ABSTRACT

An electrode system for reducing noise from an electronic signal, the system including an electrode that provides the electronic signal, and a sensor that senses motion and provides a motion signal. The electrode system includes a controller that determines a noise value based on an analysis of the motion signal, and subtracts the noise value from the electronic signal. The electrode system can reduce or eliminate motion artifact from an electronic signal that can result in misdiagnosis, prolong procedural duration and inappropriate treatment of a patient.

15 Claims, 5 Drawing Sheets

ELECTRODE SYSTEMS AND METHODS FOR REDUCING MOTION ARTIFACT

INCORPORATION BY REFERENCE

This non-provisional application claims priority under 35 U.S.C. §119 of U.S. Provisional Application No. 60/352,202, filed on Jan. 29, 2002, and entitled "Electrode Motion Artifact Reduction System." The provisional application is incorporated herein by reference in its entirety.

BACKGROUND OF THE INVENTION

1. Field of Invention

The present invention relates to electrode systems and methods for reducing motion artifact.

2. Description of Related Art

Medical practitioners use many medical field applications when diagnosing a patient. For example, the medical practitioner can use an electrocardiogram (ECG) or other monitoring, recording and analyzing systems such as electrogastrograms, electroencephalograms or electromyograms. An electrocardiogram (ECG) is a body surface manifestation of electrical potentials produced by a beating heart. The ECG is a prescribed diagnostic procedure in medicine and can be used, for example, to diagnose heart disease, identify irregular cardiac rhythms (arrhythmias), evaluate the effects of drugs, and monitor surgical procedures. The magnitude, conduction and duration of these potentials can be detected by placing an electrode on the skin of a patient.

Errors in the form of noise can occur when the ECG is performed on a patient. For example, motion artifact is noise that is introduced to the ECG signal that can result from motion of an electrode that is placed on the skin of a patient. The presence of motion artifact can result in misdiagnosis, prolong procedure duration and can lead to delayed or inappropriate treatment decisions. Thus, it is imperative to remove motion artifact from the ECG signal to prevent these problems from occurring during treatment.

Methods for reducing the effects of motion artifact in the ECG have been disclosed which focus of the skin deformation. These methods include removing the epidermal layer of the skin by abrasion, puncturing the skin in the vicinity of the electrode, and measuring skin stretch at the electrode site. The methods for skin abrasion ensure good electrical contact between the electrode and the patient's skin. In this method, an abrasive pad is mechanically rotated on the skin to abrade the skin surface before electrode placement. Moreover, medical electrodes have been used with an abrading member to prepare the skin after application of the electrode whereby an applicator gun rotates the abrading member. Methods of skin preparation that abrade the skin with a bundle of fibers have also been disclosed. The methods discussed above provide a light abrasion of the skin to reduce the electrical potential and minimize the impedance of the skin, thereby reducing motion artifacts. However, skin abrasion methods can cause unnecessary patient discomfort, prolong procedure preparation time and can vary based on operator experience. Furthermore, skin abrasions methods can lead to infection, and do not provide an effective solution to long term monitoring.

A method using an electrode that includes penetration tines to puncture the skin, and reduce skin impedance and the skin's propensity to generate motion artifact has also been disclosed. However, methods involving skin puncture can also cause the problems discussed above to occur.

A method using an electrode with a sensor incorporated in the cap to measure cable motion is also known. The cable motion is measured and is used to filter motion artifact. Electrode assemblies incorporate cable anchors to provide strain relief and decrease motion artifact caused by cable motion. Furthermore, an electrode pad inhibits cable motion. However, these devices and methods only deal with decreasing motion artifact caused by cable motion, and do not reduce or eliminate potential initiators of motion artifact caused by the electrode motion. Although some of the methods and devices disclose a sensor enclosed within the cap, the sensor is used to measure cable motion and not the electrode motion.

Devices to measure skin stretch at the electrode site, and use this information to remove motion artifact from the contaminated signal are known. A strain gauge sensor is used to measure changes in the shape of the foam pad of the ECG electrode as a measure of skin deformation and then filter this measurement. Since the sensor is attached to the foam pad of the ECG electrode, it must be disposable which increases the overall cost of the device.

An electrode assembly with a plurality of signal acquisition areas is also known whereby the plurality of signals measure the same signal and are then received by a plurality of data acquisition devices for use in comparative studies or research applications. Although the signals can be compared to each other, they are not used to decrease the noise in the signals.

A system and method for conditioning the skin by passing electrical energy through the electrodes to minimize the skin impedance has been used to reduce motion artifact. Specifically, the systems measure the changes in the impedance around the electrode site and use those measurements to reduce motion artifact. This method is used to measure the variation in the skin's impedance around the electrode site and then transfer functions to relate this measurement to the electrode signal.

As previously discussed, the systems and methods discussed above are ineffective, cause unnecessary patient discomfort, and/or are too costly to be implemented in today's health care setting. Moreover, the above systems and methods concentrate on measuring or decreasing the mechanical artifacts.

Additional methods and systems have concentrated on solving the motion artifact problem with software algorithms and filtering. For example, one system discloses a filter system for removing small amplitude, high frequency signals from an ECG signal with a low pass filter with variable cutoff frequencies which respond to detection of a QRS complex in an ECG signal. Moreover, a device and method for filtering out baseline fluctuations from an ECG by means of a high pass or band pass filter has been disclosed. Finally, an algorithm and filtering system has been disclosed which separates the ECG signal into two signals, filters one signal, and then combines the resulting signals. However, none of these systems and methods incorporate the actual known motion of the electrode, and instead rely entirely on software filtering.

Accordingly, systems and methods are needed that reduce or eliminate the problems discussed above by measuring electrode motion by using non-disposable sensors attached to a cap of an ECG lead wire and then uses this measurement to filter motion artifact.

SUMMARY OF THE INVENTION

The invention provides systems and methods that reduce or eliminate motion artifact that is produced in an electronic signal.

The invention further provides systems and methods that reduce or eliminate motion artifact from electronic signals that can result in misdiagnosis, prolong procedural duration and inappropriate treatment of a patient.

The invention further provides systems and methods that can be used during any procedure whereby the magnitude, conduction and duration of electrical potentials can be detected by placing an electrode on the skin of a patient.

The invention separately provides systems and methods that reduce or prevent patient discomfort, procedural preparation time and variation based on operator experience. Furthermore, the invention separately provides systems and methods that can be used without causing skin abrasions that can lead to infection, and can provide an effective solution to long term monitoring.

The invention separately provides systems and methods that do not require disposable sensors which increase costs associated with devices that reduce or eliminate motion artifact.

In various exemplary embodiments of the electrode systems and methods according to the invention, an electrode system includes an electrode and sensor that provide an estimate of actual motion noise along with adaptive filtering methods.

In various exemplary alternative embodiments of the electrode systems and methods according to the invention, the adaptive filtering methods transform the motion sensor output into the noise induced in electronic leads. An estimate of the noise is then subtracted from the corrupted signal resulting in an electronic signal free of motion artifact.

Additional functions, objects, advantages and features of the present invention will become apparent from consideration of the following description and drawings of exemplary embodiments.

BRIEF DESCRIPTION OF THE DRAWINGS

These and other features and advantages of the invention are described in, or are apparent from, the following detailed description of various exemplary embodiments of the systems and methods according to the invention, wherein like numerals reference like elements, and wherein.

DETAILED DESCRIPTION OF PREFERRED EMBODIMENTS

As discussed above, errors can occur in electrical medical devices used in diagnosing a patient. These errors can include motion artifact or other noise that is introduced to the electronic signal that results from motion of the electrode. While the embodiments discussed below use motion artifact as one example of an noise that can occur during an ECG, it should be appreciated that the systems and methods according to the invention can reduce any motion artifact associated with an electrode and/or lead wire without departing from the spirit and scope of the invention. Moreover, while the invention is discussed using an ECG as an example, the systems and methods discussed below can be used in many medical field applications that use an electrode system, including electrogastrograms, electroencephalograms, electromyograms or other monitoring, recording and analyzing systems.

Figure 1:
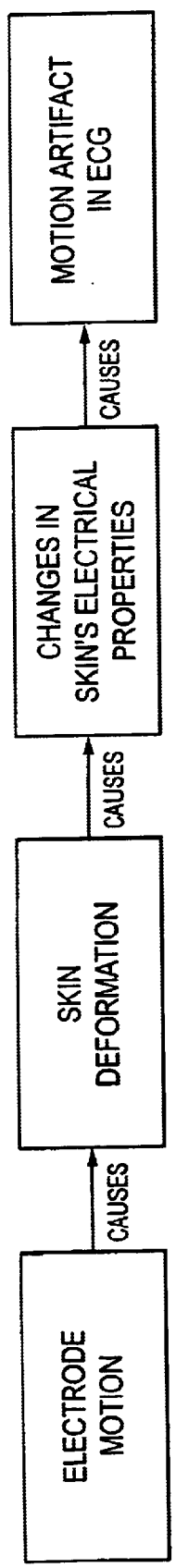
FIG. 1 is an exemplary block diagram of a cause and effect relationship between electrode motion and motion artifact.

FIG. 1 is an exemplary block diagram showing the cause and effect relationship between electrode motion and motion artifact. As shown in FIG. 1, movement of an electrode and/or lead wire used on a patient can result in deformations of the skin around the electrode site. These skin deformations alter the impedance and capacitance of the patient's skin around the sensing electrode. As a result, the impedance and capacitance changes are sensed by the ECG electrode and cause motion artifact in the ECG.

The motion artifact is noise that results in a contaminated signal being received from the electrode, and is particularly a problem in cases where it is necessary to make such recordings while the patient is engaged in activity. These artifacts arise from the skin deformation, which may be produced by forces transmitted through the skin electrode interface or by forces on the skin generated by movement of the patient.

Figure 2A:
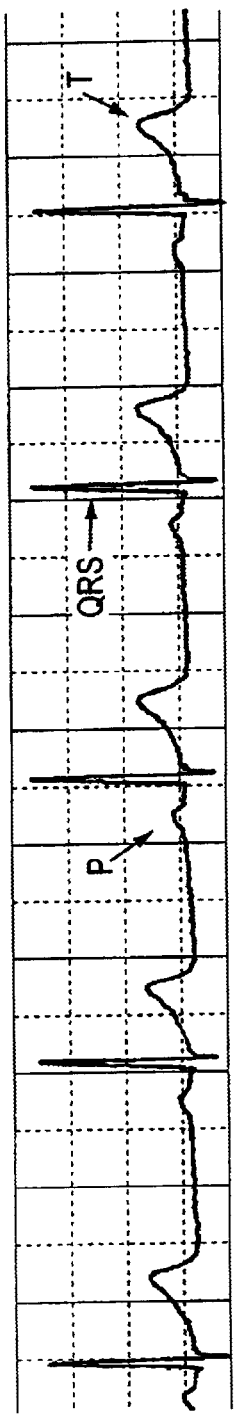
FIGS. 2A–C illustrate exemplary diagrams of a noise free ECG tracing, an ECG tracing with moderate motion artifact and an ECG tracing with severe motion artifact.

FIG. 2A illustrates an exemplary diagram of a noise free ECG tracing. As shown in FIG. 2A, the P, QRS and T waveforms are clearly distinguished in the ECG tracing because no noise is present. The P and QRS waveforms are the ECG manifestations of contraction of the atrial and ventricular myocardium, respectively. The T waveform is the ECG manifestation of the relaxation of the ventricular myocardium. By using the noise free tracing shown in FIG. 2A, any misdiagnosis, prolonged procedural duration and inappropriate treatment of a patient by a medical practitioner can be avoided.

Figure 2B:
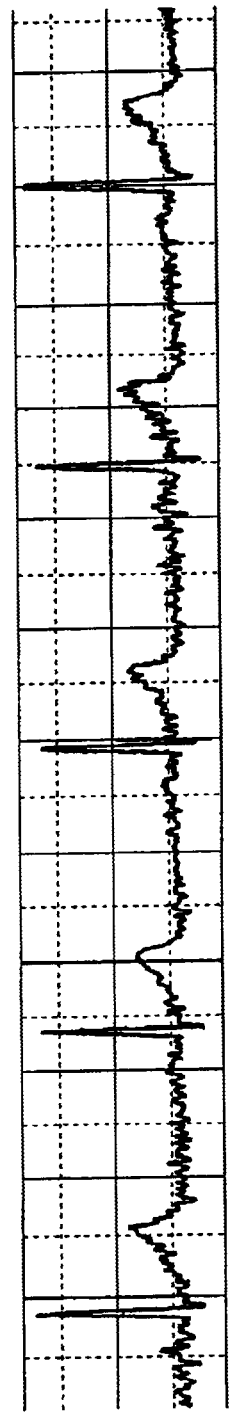
Figure 2C:
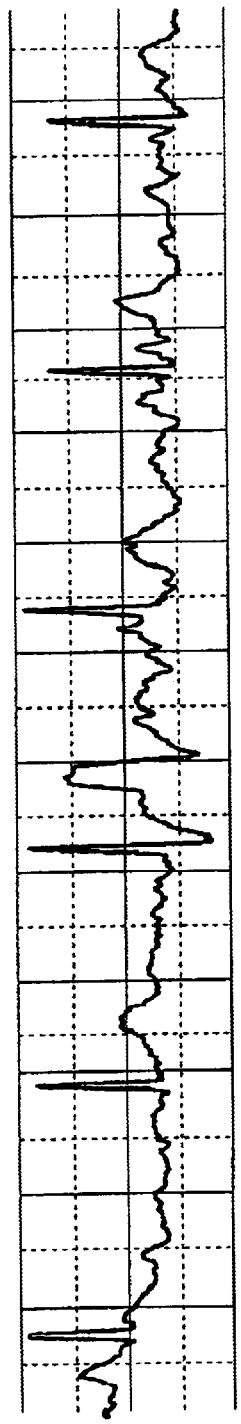

However, the motion artifact can produce large amplitude signals on the ECG. Moreover, the motion artifact can be very prevalent during ambulatory (Holter) monitoring and stress test recording. FIG. 2B illustrates an exemplary diagram showing an ECG tracing with moderate motion artifact within the tracing. As shown in FIG. 2B, the frequency spectrum of the motion artifact can overlap the ECG frequency spectrum. Thus, because the motion artifact can resemble the P, QRS and T waveforms, the motion artifact can be difficult to remove from the ECG. FIG. 2C shows an exemplary diagram of an ECG tracing with severe motion artifact. The motion artifact in both FIGS. 2B and 2C masks the P waveform, and resembles the QRS complex in FIG. 2C. Accordingly, as discussed above, the motion artifact in the ECG recording can result in misdiagnosis, prolong procedure duration, and may lead to delayed or inappropriate treatment decisions.

By measuring the electrode motion using non-disposable sensors attached to, or incorporated into, the ECG lead wire cap in accordance with the systems and methods of the invention, the origin of the motion artifact is accurately measured. The electrode system uses sensors that provide a reference of the actual ECG motion noise along with adaptive filtering methods. The adaptive filtering methods transform the motion sensor output into the noise induced in the ECG leads. An estimate of the noise is then subtracted from the corrupted ECG signal resulting in an ECG signal free of motion artifact.

Figure 3:
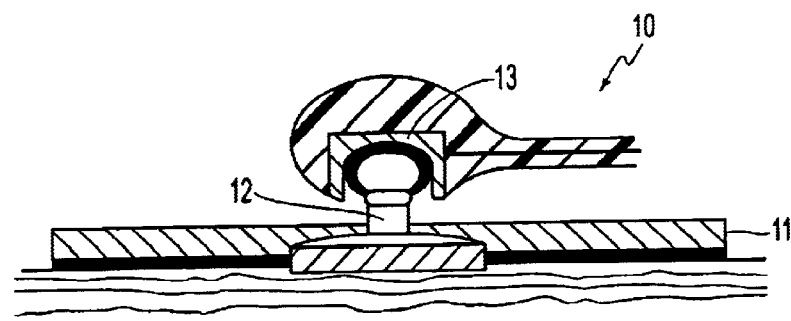
FIG. 3 is an exemplary block diagram of an electrode system according to the systems and methods of the invention.

FIG. 3 is an exemplary block diagram of an electrode system 10 according to the systems and methods of the invention. As shown in FIG. 3, an electrode system 10 includes a electrode patch 11, an electrode 12, and a sensor 13. The electrode patch 11 can be constructed of any material that readily conforms to the local shape of the skin without departing from the spirit and scope of the invention. For example, the ECG electrode patch 11 can be constructed of rubber or plastic. The patch 11 has a front surface that engages the skin of the patient and a rear surface. A central recess is provided in the patch (not shown in the figure). The front surface of the patch 11 is placed on the skin of the patient and is maintained on the skin with an adhesive. It should be appreciated that any known adhesive that acts as a fastener to fasten the patch 11 onto the skin of the patient can be used according to the systems and methods of the invention.

The electrode 12 in FIG. 3 can be any device that can conduct electricity including semiconducting material. For example, the electrode 12 can be a device composed of a metallic substance or a polymer, such as an organic polymer. It should be appreciated that any known substance that acts as a conductor or semiconductor can be used as the electrode 12 according to the systems and methods of the invention. The electrode 12 has a sensing end and a connector end and passes through the central recess of the patch so that the sensing end resides within the central recess. The electrode 12 can be positioned so that the sensing end of the electrode 12 is in close proximity to the patient's skin when the patch 11 is in contact with the skin. The central recess can be filled with a conductive paste to provide a conductive path between the skin and the sensing end of the electrode 12. The connector end of the electrode 12 can pass beyond the rear surface of the patch 11 making it accessible to a clip that attaches to the connector end of the electrode 12. The clip can then be attached to a lead wire that connects to a patient monitoring device. The top part of the connector end is generally referred to as the cap.

The sensor 13 in FIG. 3 can be coupled to the cap and can be used to sense motion. The sensor 13 can be coupled to the cap can by any fastener device or composition, such as a mechanical fastener, bonding, sealant or by other known attachment devices and compositions. It should be appreciated that the sensor 13 can be any type of sensor that can measuring motion such as an accelerometer, magnetic sensor, or strain gauges without departing from the spirit and scope of the invention. Motion can be measured in one, two, and/or three dimensions along various axis. By increasing the number of dimensions of motion measured, the accuracy of the electrode motion measurement correspondingly increases.

Figure 4:
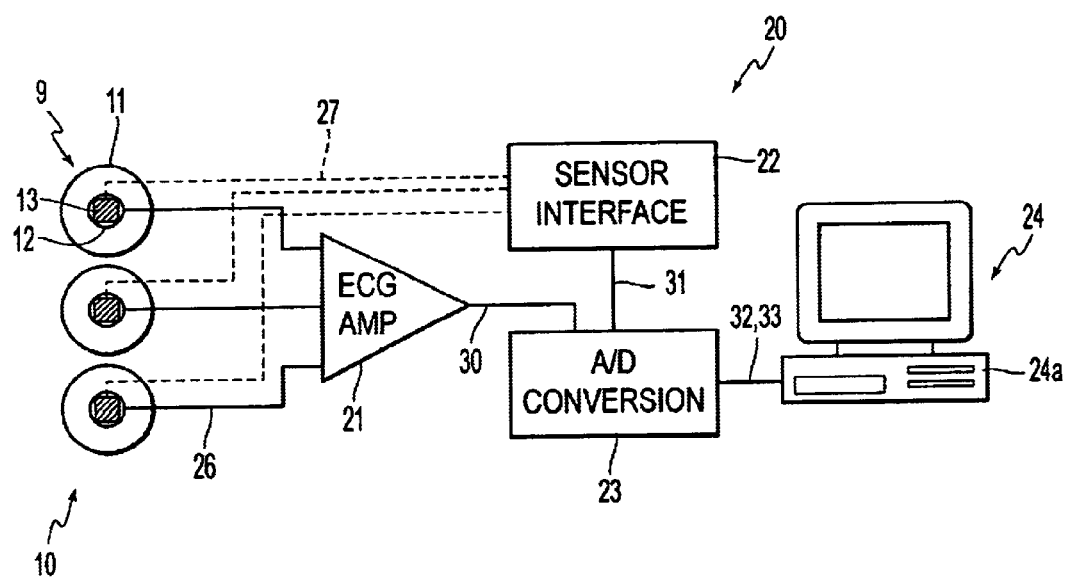
FIG. 4 is an exemplary diagram showing a location of a sensor in an electrode system that can be used according to the systems and methods of the invention.

FIG. 4 is an exemplary diagram showing a location of a sensor 13 in the electrode system 10 that can be used according to the systems and methods of the invention. The electrode system 10 can be used with a patient monitoring system 20 which employs at least one assembly 9 having electrodes 12 for monitoring physiological signals produced from the electrode system discussed above. Each of the electrode assemblies 9 within the electrode system 10 can include a motion sensor 13 coupled to the electrode cap for the generation of electrode motion signals. As shown in FIG. 4, the white circle represents the electrode patch 11, the gray circle represents the electrode cap 12 and the black square represents the motion sensor 13.

A patient monitoring system 20, as shown in FIG. 4, can have an amplifier 21 that receives the physiological signals from each of the electrode assemblies 9 through links 26 and generates amplified differential physiological signals 30. A sensor interface 22 can be used to receive the signals from the motion sensors 13 of each of the electrode assemblies 9 through links 27 in order to provide processed motion signals 31. Moreover, a multiplexer (not shown in the figure) can be provided which selectively passes the amplified differential physiological signals 30 and the processed motion signals 31 to an A/D converter 23, which in turn digitizes the signals received to provide digital differential physiological signals 32 and digital motion signals 33.

As shown in FIG. 4, a controller 24 can be included with the electrode system 10 that has an adaptive noise cancellation circuit or routine 24a such as Least Means Squared (LMS), Recursive Least Squares (RLS), and Lattice algorithms. It should be appreciated that any known noise cancellation circuit or routine can be used with the electrode system 10 without departing from the spirit and scope of the invention. The adaptive noise cancellation circuit or routine 24a receives the digital signals 32 and 33, and then the controller combines the digital differential physiological signals 32 and the digital deformation signals 33 to provide filtered digital physiological signals. An example of adaptive filtering an ECG signal to reduce the noise in the signal is disclosed in "Applications of Adaptive Filtering to ECG Analysis: Noise Cancellation and Arrhythmia Detection" by Thakor et al., which hereby incorporated by reference in its entirety.

Figure 5:
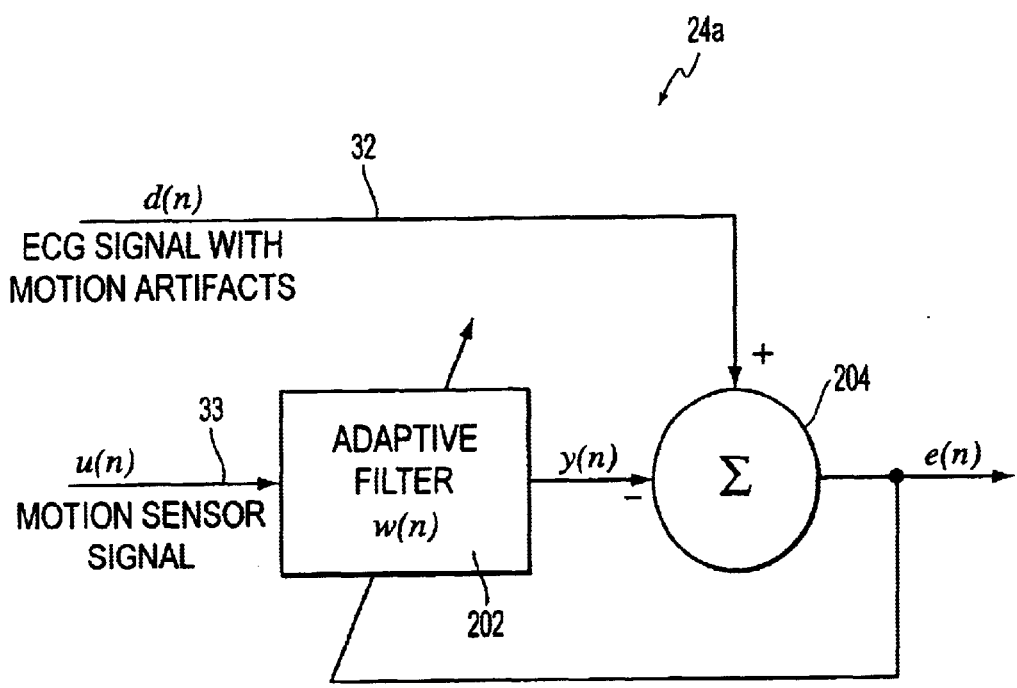
FIG. 5 is an exemplary diagram of a filter circuit that can be used according to the systems and methods of the invention.

FIG. 5 is an exemplary diagram of a adaptive noise cancellation circuit 24a that can be used according to the systems and methods of the invention. In FIG. 5, an adaptive filter w(n) 202 can be represented as an M×1 array of filter coefficients, where M is the order of the filter. The adaptive filter w(n) 202 filters the motion sensor signal u(n) from the motion sensor 13 into an estimate y(n) of the motion noise in the ECG signal. The estimate y(n) is then subtracted in a summarizer 204 from the noisy ECG signal d(n), which has been sent from the electrode 12, to produce the output e(n). The output e(n) can be used as feedback to update the adaptive noise cancellation circuit 24a. In this configuration, the filter w(n) 202 adapts to minimize the value of e(n). An example of a process that can be used with the filter shown in FIG. 5 is shown in Equations (1)–(3) below, where:

$$y(n) = W^T(n)u(n) \tag{1}$$

$$e(n) = d(n) - y(n) \tag{2}$$

$$w(n+1) = w(n) + \mu u(n) e(n) \tag{3}$$

In Equation (1), $w^T(n)$ is the transpose of w(n), and u(n) is defined in Equation (4).

$$u(n) = \begin{bmatrix} u(n) \\ u(n-1) \\ \vdots \\ u(n-M+1) \end{bmatrix} \tag{4}$$

It should be appreciated that the adaptive noise cancellation circuit 24a shown in FIG. 5 can be modified to reduce the removal of desired electrical signal components and allow various values of u and M to be used in the process described above. For example, frequency analysis of a noisy ECG signal along communication link 32 in FIG. 5 can show that the QRS signal has a much higher frequency content that that of the motion signal noise on communication link 33. Thus, a lowpass filter can be positioned along communication link 32 in FIG. 5, prior to the summarizer 204, to reduce the QRS signal with motion artifacts without modifying the motion signal noise.

Figure 6:
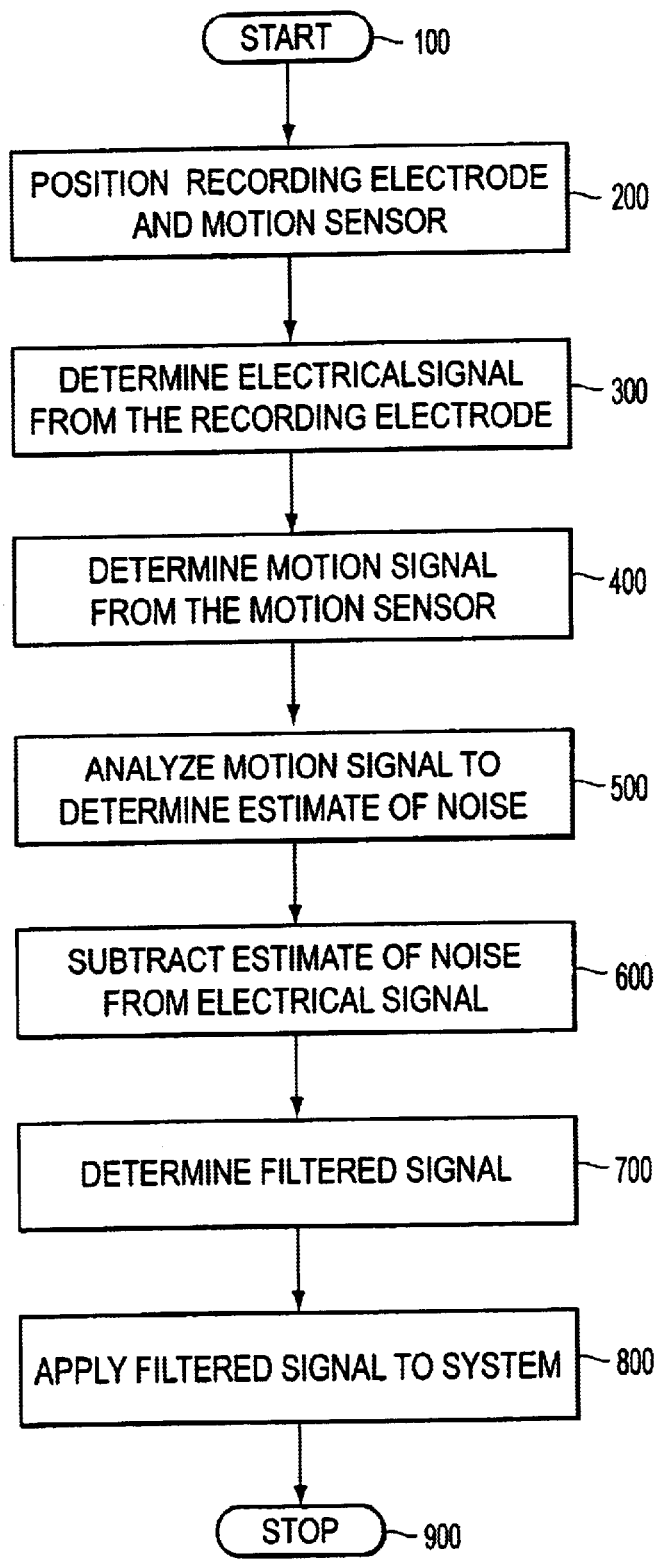
FIG. 6 is an exemplary flowchart showing a method of filtering motion artifact from an ECG tracing that can be used according to the systems and methods of the invention.

FIG. 6 is an exemplary flowchart showing a method of filtering noise, i.e., motion artifact, from an electronic signal that can be used according to the systems and methods of the invention. In this embodiment, the method of eliminating the motion artifact uses signals from physiological recording electrodes that are mounted on the skin of the patient. At least one motion sensor is coupled to a recording electrode and connected to the patches which are then mounted on the skin of the patient. Specifically, after beginning in step 100, a pair of skin mounted physiological recording electrodes are attached in step 200 to the skin of a patient with electrode patches. Then, electrical signals, for example, differential signals, from each recording electrode within the pair are determined in step 300. Motion signals from the motion sensors are then determined in step 400 and an adaptive noise cancellation analysis is made of the motion signals in step 500 in order to determine an estimate of noise from the differential signals. In step 600, the estimate of noise is subtracted from the differential signals so that a filtered differential physiological signal can be determined in step 700 from the analysis of these signals. Then, in step 800, the filtered signal can be applied to an ECG system to reduce or eliminate motion artifact before the process stops in step 900. The analysis can be done by employing the adaptive filtering techniques discussed above.

In the illustrated embodiments, the controller is implemented with a general purpose processor. It will be appreciated by those skilled in the art that the controller can be implemented using a single special purpose integrated circuit (e.g., ASIC) having a main or central processor section for overall, system-level control, and separate sections dedicated to performing various different specific computations, functions and other processes under control of the central processor section. The controller can be a plurality of separate dedicated or programmable integrated or other electronic circuits or devices (e.g., hardwired electronic or logic circuits such as discrete element circuits, or programmable logic devices such as PLDs, PLAs, PALs or the like). The controller can be suitably programmed for use with a general purpose computer, e.g., a microprocessor, microcontroller or other processor device (CPU or MPU), either alone or in conjunction with one or more peripheral (e.g., integrated circuit) data and signal processing devices. In general, any device or assembly of devices on which a finite state machine capable of implementing the procedures described herein can be used as the controller. A distributed processing architecture can be used for maximum data/signal processing capability and speed.

While the invention has been described with reference to preferred embodiments thereof, it is to be understood that the invention is not limited to the preferred embodiments or constructions. To the contrary, the invention is intended to cover various modifications and equivalent arrangements. In addition, while the various elements of the preferred embodiments are shown in various combinations and configurations, which are exemplary, other combinations and configurations, including more, less or only a single element, are also within the spirit and scope of the invention.

What is claimed is:

1. An electrode system for reducing motion artifact from an electronic signal, the system comprising:

an electrode that provides an electronic signal;

a sensor that senses electrode motion and provides a motion signal; and a controller that determines a noise value based on an analysis of the electronic signal and the motion signal, and subtracts the noise value from the electronic signal.

2. The electrode system of claim 1, further comprising the electrode and the sensor coupled together and connected to a patch that is placed on the skin of a patient.

3. The electrode system of claim 1, wherein the sensor senses the motion in at least one dimension.

4. The electrode system of claim 1, wherein the controller is part of a patient monitoring system.

5. The electrode system of claim 4, the controller uses a noise cancellation circuit or routine to subtract the noise value from the electronic signal.

6. The electrode system of claim 1, further comprising a plurality of electrodes that produce a plurality of electronic signals that are differential physiological signals of a human being.

7. A method for reducing motion artifact from an electronic signal, comprising:

measuring an electronic signal through an electrode;

sensing electrode motion through a sensor;

generating a motion signal based on the sensed electrode motion;

determining a noise value based on an analysis of the electronic signal and the motion signal; and subtracting the noise value from the electronic signal.

8. The method of claim 7, further comprising coupling the electrode and the sensor together and connecting them to a patch that is placed on the skin of a patient.

9. The method of claim 7, further comprising sensing the motion in at least one dimension.

10. The method of claim 7, wherein a patient monitoring system determines the noise value based on the analysis of the electronic signal and motion signal, and subtracts the noise value from the electronic signal.

11. The method of claim 10, the patient monitoring system uses a noise cancellation circuit or routine to subtract the noise value from the electronic signal.

12. The method of claim 7, further comprising producing a plurality of electronic signals that are differential physiological signals of a human being.

13. A method for reducing motion artifact from differential electronic signals, comprising:

measuring differential electronic signals produced by at least two recording electrodes;

sensing electrode motion through a sensor associated with each of the at least two recording electrodes;

generating motion signals based on the sensed electrode motion of each of the at least two recording electrodes;

analyzing the motion signals;

determining noise values based on the analysis of the motion signals; and subtracting the noise values from the differential electronic signals.

14. The method of claim 13, further comprising determining the motion signals based on at least one dimension.

15. The method of claim 13, further comprising producing a plurality of differential signals that are physiological signals of a human being.

* * * * *